United States Patent
Matschke

(10) Patent No.: US 6,700,128 B2
(45) Date of Patent: Mar. 2, 2004

(54) APPARATUS AND METHOD FOR SIMULTANEOUSLY GERMICIDALLY CLEANSING BOTH AIR AND WATER

(75) Inventor: Arthur Matschke, Bridgewater, CT (US)

(73) Assignee: Molecucare, Inc., New Milford, CT (US)

( * ) Notice: Subject to any disclaimer, the term of this patent is extended or adjusted under 35 U.S.C. 154(b) by 168 days.

(21) Appl. No.: 10/037,313

(22) Filed: Jan. 4, 2002

(65) Prior Publication Data

US 2002/0088945 A1 Jul. 11, 2002

Related U.S. Application Data

(63) Continuation-in-part of application No. 09/654,725, filed on Sep. 5, 2000, now Pat. No. 6,337,483, which is a continuation-in-part of application No. 09/499,597, filed on Feb. 7, 2000, now Pat. No. 6,228,327, which is a continuation-in-part of application No. 09/112,500, filed on Jul. 9, 1998, now Pat. No. 6,022,511.

(51) Int. Cl.[7] .................................................. A61L 9/20

(52) U.S. Cl. .................. 250/432 R; 250/435; 250/436; 422/24; 422/121

(58) Field of Search ............................... 250/436, 435, 250/432 R, 455.11; 422/24, 121

(56) References Cited

U.S. PATENT DOCUMENTS

| 3,970,426 A | * | 7/1976 | Stark et al. | 422/24 |
| 3,994,686 A | * | 11/1976 | Rauser et al. | 422/24 |
| 6,337,483 B1 | * | 1/2002 | Matschke | 250/432 R |

* cited by examiner

*Primary Examiner*—Jack Berman
(74) *Attorney, Agent, or Firm*—Bazerman & Drangel P.C.

(57) ABSTRACT

A germicidal UV chamber for use on air passing through a duct system, such as a central air system which replace one or more sections of the duct and, in essence, becomes part of the duct work. Each chamber is in the form of one or more ellipsoid sections which focus the energy uniformly throughout the chamber. The UV lamp is in the form of a helix around the center line of the chamber. Its pitch may very along its length so as to concentrate the UV radiation towards the center of the chamber. A UV transparent conduit may be positioned in the center of the coils of the helical UV lamp to convey a liquid through the lamp.

9 Claims, 12 Drawing Sheets

APPARATUS AND METHOD FOR SIMULTANEOUSLY GERMICIDALLY CLEANSING BOTH AIR AND WATER

This application is a continuation-in-part of pending U.S. patent application Ser. No. 09/654,725, filed Sep. 5, 2000, now U.S. Pat. No. 6,337,483, which in turn is a continuation-in-part of Ser. No. 09/499,597 filed Feb. 7, 2000, now U.S. Pat. No. 6,228,327, issued May 8, 2001 which in turn is a continuation-in-part of Ser. No. 09/112, 500 filed Jul. 9, 1998, now U.S. Pat. No. 6,022,511, issued Feb. 8, 2000.

BACKGROUND OF THE INVENTION

Airborne bacteria or other microorganisms permeate the air we breath and the water we drink. Some of these microorganisms with which we share our environment cause disease. Medical environments, such as hospitals, have a high degree of pathogens in the air and water and highly susceptible, weakened patients. The existence of biological weapons of mass destruction require protection of command centers, barracks, ships, and other closed environments against biological agents. Today's modern sealed high-rise structures with central air conditioning and heating, through duct systems, need protection from the spread of disease among its occupants and from colonies of microorganisms which may live in the duct and water system. Today, biologic protection is necessary on the battlefield and in the workplace, the hospital and the home.

Much effort has gone into trying to destroy atmospheric pathogens with only limited success. It has long been recognized that pathogens can be destroyed in the air if they are irradiated with ultraviolet (UV) light at a wavelength of 253.7 nanometers (Germicidal Wavelength). In order for the UV light to kill microorganisms, the UV rays must directly strike the microorganisms for a sufficient time. Because of the absolute necessity for antiseptic surroundings, UV lamps of the required Germicidal Wavelength are often used in operating rooms, wards, and nurseries of hospitals.

The exposure to UV light necessary to kill microorganisms is a product of time and intensity. However, due to the dangers to humans of irradiation from wide-spread use of UV lamps, exposure to UV light has been limited by government regulations. The current occupant exposure limit (ACGIH, NIOSH standard) for 254 m ultraviolet germicidal wavelength ceiling fixtures is 6000 $\mu$watts seconds/cm$^2$ in one eight hour day. Thus, the maximum allowed intensity per second is 0.2 $\mu$W/cm$^2$. At this intensity, eight hours at the allowed exposure level is required to gain a 90% kill of *Mycobacterium tuberculosis* (90% kill-value= 6200 $\mu$watts/cm$^2$) at head height. For 100% kill using the same standard, the value is 10,000 $\mu$watts/cm$^2$, requiring 13.89 hours of exposure. The required low intensity, and resulting long exposure times, permit migration of microorganisms out of range of the UV lamp and result in accumulation of microorganisms which survive the UV lamp in the room. Increasing air circulation does not increase exposure of microorganisms. It only moves organisms past the UV lamp without sufficient exposure.

To overcome these problems there have been various attempts to circulate air passed UV sources in enclosures which acts to shield the UV irradiation from the room's occupant. Usually, such systems are free-standing, or wall or ceiling mounted devices which circulate the air in a single room through the enclosure and, accordingly, whose protection is confined to that room. See, for example, U.S. Pat. No. 5,330,722 to Pick, which discloses a germicidal air purifier which draws air through a chamber in which there is mounted an ultraviolet source which acts to kill microorganisms caught in the filter structure. Similarly, U.S. Pat. No. 5,612,001 to Arthur L. Matschke, discloses a germicidal air cleansing enclosure having an internal ellipsoid chamber which contains UV lamps along the major axis of the ellipsoid. The unit is free-standing and treats air in a single room.

While a system such as that disclosed in U.S. Pat. No. 5,612,001 to Arthur L. Matschke, may be highly effective to cleans the contents of a single room, normal air conditioning and heating ducts would continue to allow circulation of untreated air into and out of a room. This allows untreated air containing pathogens from another room, or in the duct system, to enter the room and come into contact with humans before being treated and allow a certain amount of pathogens in a room to enter the duct system prior to being treated by the free-standing unit.

Various attempts have been made to place ultraviolet light sources in duct systems to germicidally cleans fluids such as air as they pass through the duct system. See, for example, U.S. Pat. No. 5,635,133 to Glazman, U.S. Pat. No. 5,200,156 to Wedekamp and U.S. Pat. No. 5,107,687 to Candelares. Each of these patents disclose an ultraviolet irradiation source in a duct to cleanse a fluid traveling through a duct of uniform diameter. The UV source is at right angles to the duct walls and UV energy is directed at least in part along the path of fluid flow. Thus, the level of ultraviolet energy varies along the flow path. As a result, the air circulated past the UV lamps in the prior art receive an uneven distribution of ultraviolet energy and a rapid diminution of energy levels outside the immediate area of the UV source. The grandparent of the present patent application, now U.S. Pat. No. 6,022,511, to Matschke, discloses an ellipsoidal, ultraviolet reflective chamber mounted in a duct system which exposes the air passing through the chamber to sufficient UV energy to germicidally cleanse all of such air. However, it does not provide the means for treating water in the same closed environment.

Bacteria or other microorganisms not only permeate the air we breath but also the water we drink. Much effort has gone into trying to limit or destroy water-borne pathogens. It has long been recognized that pathogens can also be destroyed in water if they are irradiated with ultraviolet (UV) light of a wavelength of 253.7 nanometers. In order for the UV light to kill microorganisms, and particularly pathogens, the rays must directly strike them. U.S. Pat. No. 5,874,741 to Matschke discloses an ellipsoid, ultraviolet reflective chamber to expose water passing through the chamber to sufficient UV energy to germicidally cleanse all of such water.

Conventional UV lamps for germicidal applications are normally in the form of elongated straight tubes similar in appearance to conventional florescent lights. Such lamps are not optimal for use in ellipsoidal chamber as they do not maximize the energy efficiency of the system as a whole.

SUMMARY OF THE PRESENT INVENTION

It is an object of the present invention to use as a source of ultra violet radiation in an ellipsoid UV chamber, a lamp in the form of a helix whereby the UV source is concentrated in the center of the chamber so as to lengthen the path to initial reflection in a chamber, thereby increasing system efficiency.

The present invention is a germicidal chamber which uniformly irradiates all of the air passing through a duct system in which it is mounted, such as a central air system. The chamber replaces one or more sections of the duct and, in essence, becomes part of the duct work. The chamber has running along the chamber's longitudinal axis an ultraviolet transparent pipe through which water or other fluids may pass. The ultraviolet transparent pipe is attached at or near both ends of the ultraviolet chamber to conventional pipes which passes through the wall either of the duct or the chamber and form part of the fluid circulatory system, such as a buildings water supply.

Each chamber is in the form of one or more ellipsoid sections which focus the energy uniformly throughout the chamber. A sphere is a form of ellipsoid and can be used in carrying forward the present operation. The chamber is connected to the duct so that all air drawn into the duct system must pass through the chamber. To accomplish this, each chamber is integral with the duct forcing all of the air in the duct on the upstream side to pass through the chamber. In order to eliminate back pressure which might arise from any impediment to the flow of air through the chamber while allowing reflection of all of the ultraviolet radiation back into the chamber, a grille formed from concentrical ellipsoid sections is positioned at each end of the chamber so that substantially all of the ultraviolet radiation is reflected back into the chamber while allowing relatively unimpeded flow of the air through the chamber.

The dispersion of ultraviolet light in the chamber and its energy efficiency can be improved by the use of a helically wound ultraviolet light source positioned around the major axis of the chamber in the center of the chamber. The helically wound ultraviolet light source may be positioned around the ultraviolet transmission pipe carrying a fluid to be treated. The geometric center point of the chamber is the point within the chamber from which light will travel the greatest distance before a first reflection, incident with the wall and, thus, the first absorption of energy. Thus, the efficiency of the light source decreases as the point of origin of the light source moves away from the center of the axis of the ellipsoid chamber as a product of the energy absorption and the subsequent infinite reflections through the enclosure. In the present invention, the helical light source is concentrated towards the center of the chamber to increase the efficiency in the even distribution of ultraviolet light throughout the chamber.

DESCRIPTION OF THE PREFERRED EMBODIMENT

Figure 1:
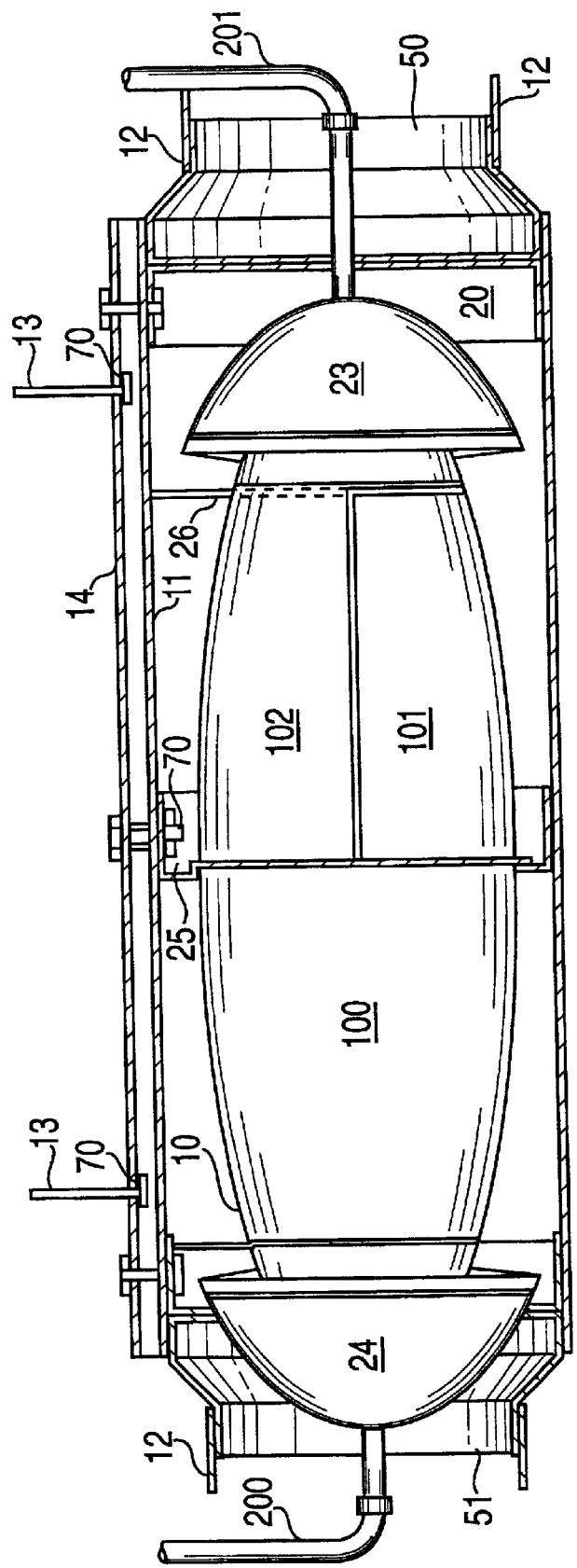
FIG. 1 is a partial cut-away front view of a chamber, in accordance with the present invention, with the shell wall partially removed.

In the present invention, the duct work of a central air system is modified to replace a portion of the duct with an ellipsoidal UV chamber 10 which becomes part of the central air duct system. Air is normally circulated through the central air system including through the chamber 10 by the HVAC fan.

The germicidal cleansing chamber 10 is mounted within a shell 11 connected to an air duct 12. The shell 11 can be used to insulate the chamber from extremes of temperature and provide alternatives for finishes to give the chamber 10 an appearance that will allow it to be hung under the ceiling. The shell 11 has mounted on it a mounting spine 14. The spine 14 is of sufficient cross-section and strength to carry the chamber 10 and may be U-shaped to allow positioning and proper mounting of the shell 11. The spine 14, and thus shell 11 and germicidal cleansing chamber 10, are mounted to the ceiling by conventional mounting means such as suspension rods, cables or straps 13. Each of the mounting means 13 are attached to the mounting spine 14 by conventional means such as nut 70.

At either end of the elliptical central portion 16 of chamber 10 are end caps 23 and 24. The central portion 16 of the chamber 10 may be composed of a number of sections 100, 101, and 102 to allow access into the interior of the chamber 10. The central portion 16 and the end caps 23 and 24 may be made from spun aluminum or formed from a molded material having aluminum or other highly UV reflective material deposited on the interior.

Figure 2:
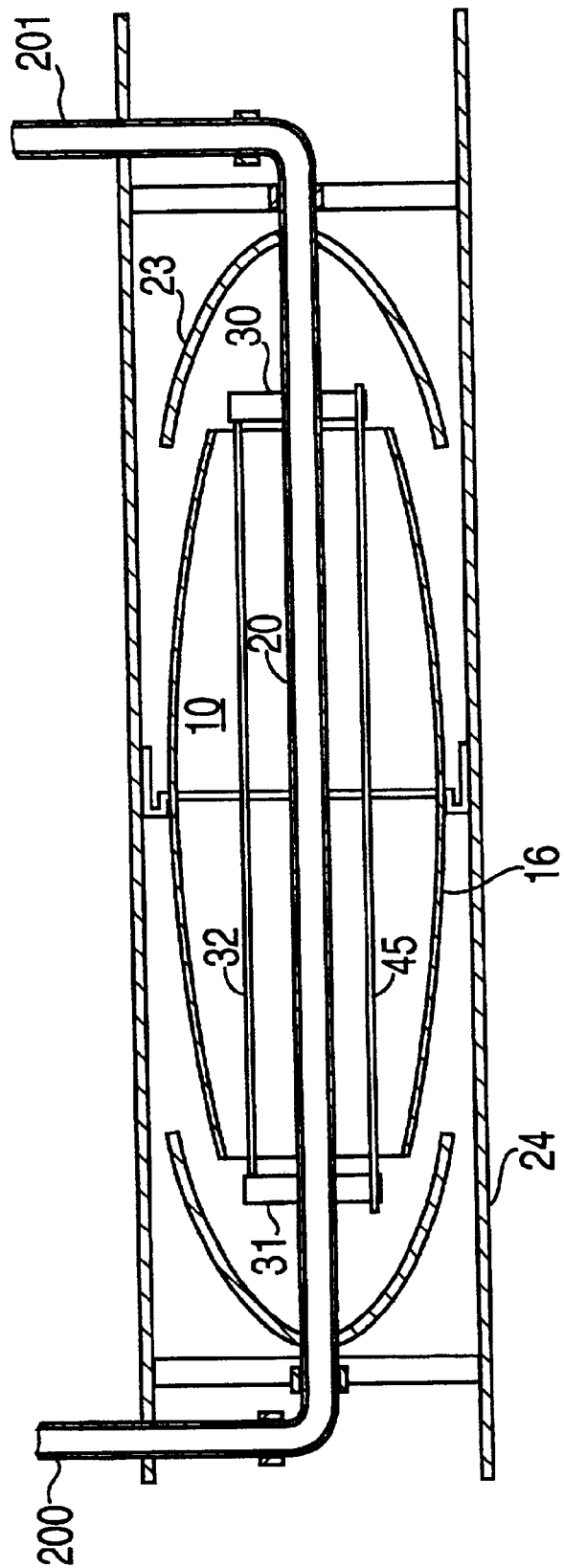
FIG. 2 is a cross-sectional view of the chamber FIG. 1.

The central portion 16 of the chamber 10 is an ellipsoid. The end caps 23 and 24 are displaced paraboloids which share a foci with the elliptical chamber. Normally, when mounted in a duct, it will be in the form of an elongated chamber as seen in FIGS. 1 and 2. However, the ellipsoid may be a sphere.

The bulkhead 25 is in sealed engagement with both the shell 11 and the central portion 16 of the chamber 10 at the mid-point of the central portion 16. As air is drawn into the duct system, it will be pass through the chamber 10, entering in the space between the end cap 23 and central portion 16. Since the chamber 10 can be mounted in existing duct systems, the air will be drawn into the chamber 10 by the circulation system of the duct system, such as a building HVAC fan.

Mounted in the chamber 10 are mounting rings 30 and 31 between which UV light sources 32 are positioned. Also attached to the mounting rings 30 and 31 are positioning rods 45 which hold the mounting rings 30 and 31 in their respective positions. For clarity of the drawings, only one UV light source 32 and one positioning rod 45 is shown. The number of UV light sources will be determined by the overall requirements of the system. The mounting rings 30 and 31 include an interior circuit board (not shown) protected by the structure of the mounting rings 30 and 31 from UV irradiation.

The chamber may be simply located in an existing duct system at a return vent or elsewhere. Adapters 50 and 51 on either side of shell 11 mate the chamber to a duct system preferably at or near a return air register.

Passing down the center of the chamber 10 is a UV transparent conduit 20. The conduit 20 is connected by conventional means to a conventional inlet pipe 200 and outlet pipe 201. Water or other fluids to be germicidally cleansed flow from the inlet pipe 200 through the chamber 10 and out the outlet pipe 201. The direction of flow can be reversed without effecting the cleansing efficiency. Pipes 200 and 201 pass through the duct walls 12 and are attached to the water distribution system. The water distribution system should be of such a design that only treated water can leave the pipes for use. The conduit 20 is shown positioned between the end caps 23 and 24. Alternatively, the UV transparent conduit 20 may enter and leave the chamber 10 through its central position 16 (not shown).

Because of the elliptical configuration of the body portion in conjunction with the effect of the parabolic end caps, the UV light generated by the UV light source is evenly dispersed throughout the extended length of the chamber 10. Any point in the chamber 10 receives the same quantity of UV light in all directions as any other point within the chamber 10. The formation of the walls of the chamber 10, by spinning and the qualities of aluminum from which it is spun, acts to ensure the greatest part of the energy generated by the UV light sources 32 is reflected back into the chamber 10 rather than being absorbed by the walls of the chamber. The effect of UV irradiation on a microorganism is dependent on both UV intensity and length of time of exposure to the UV irradiation. Since the walls are highly reflective, the irradiation intensity created reaches a steady state which is substantially greater than the output of the lamps and, because of the configuration, is evenly distributed through the chamber.

Figure 3:
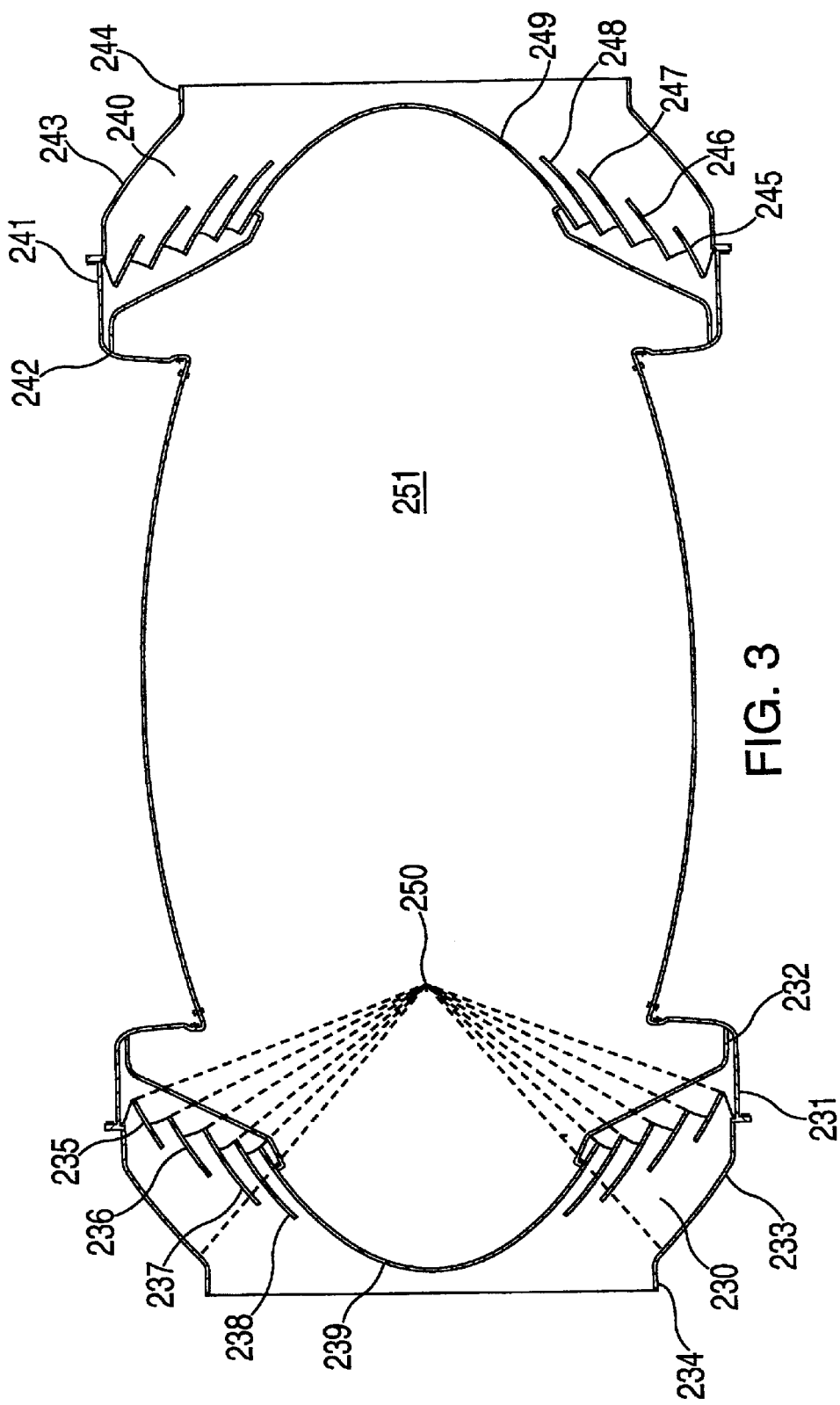
FIG. 3 is a cross-sectional view of another embodiment of the chamber of the present invention, not showing its ultraviolet light source or the ultraviolet transparent pipe, having a reflective grille at either end of the chamber.
Figure 4:
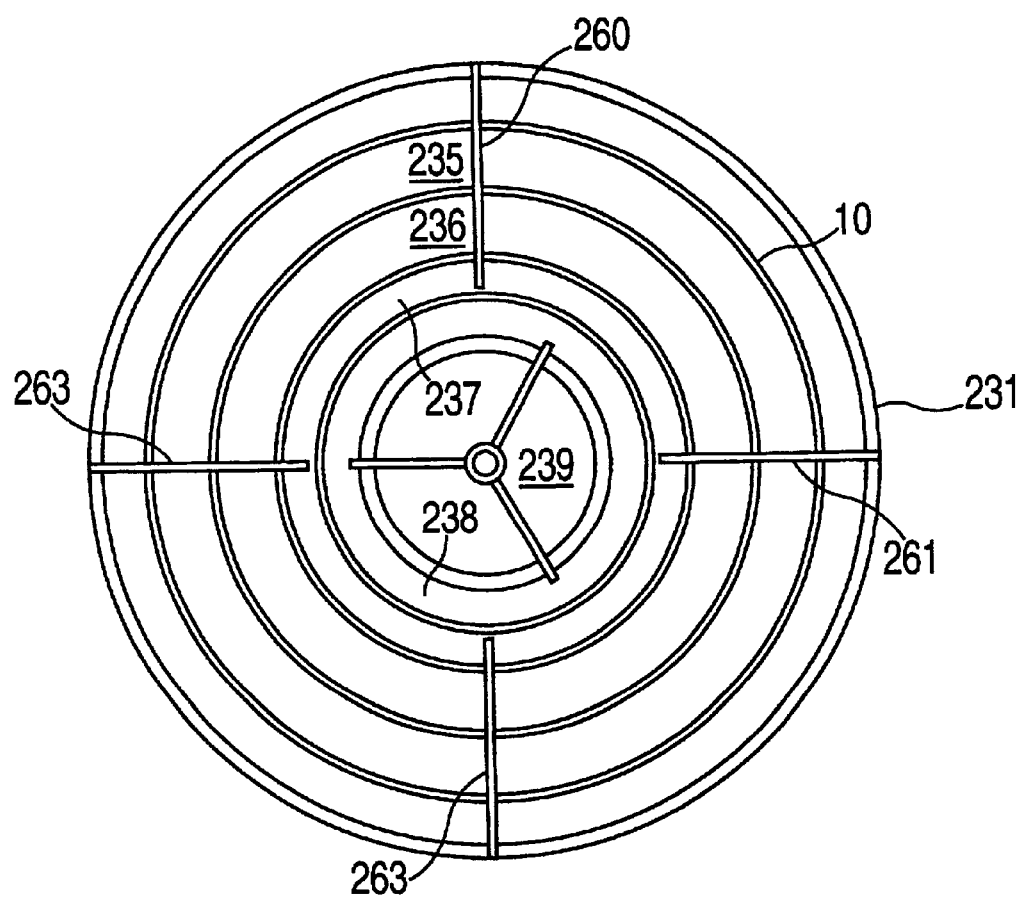
FIG. 4 is a sectional view at plane A—A of FIG. 3
Figure 5:
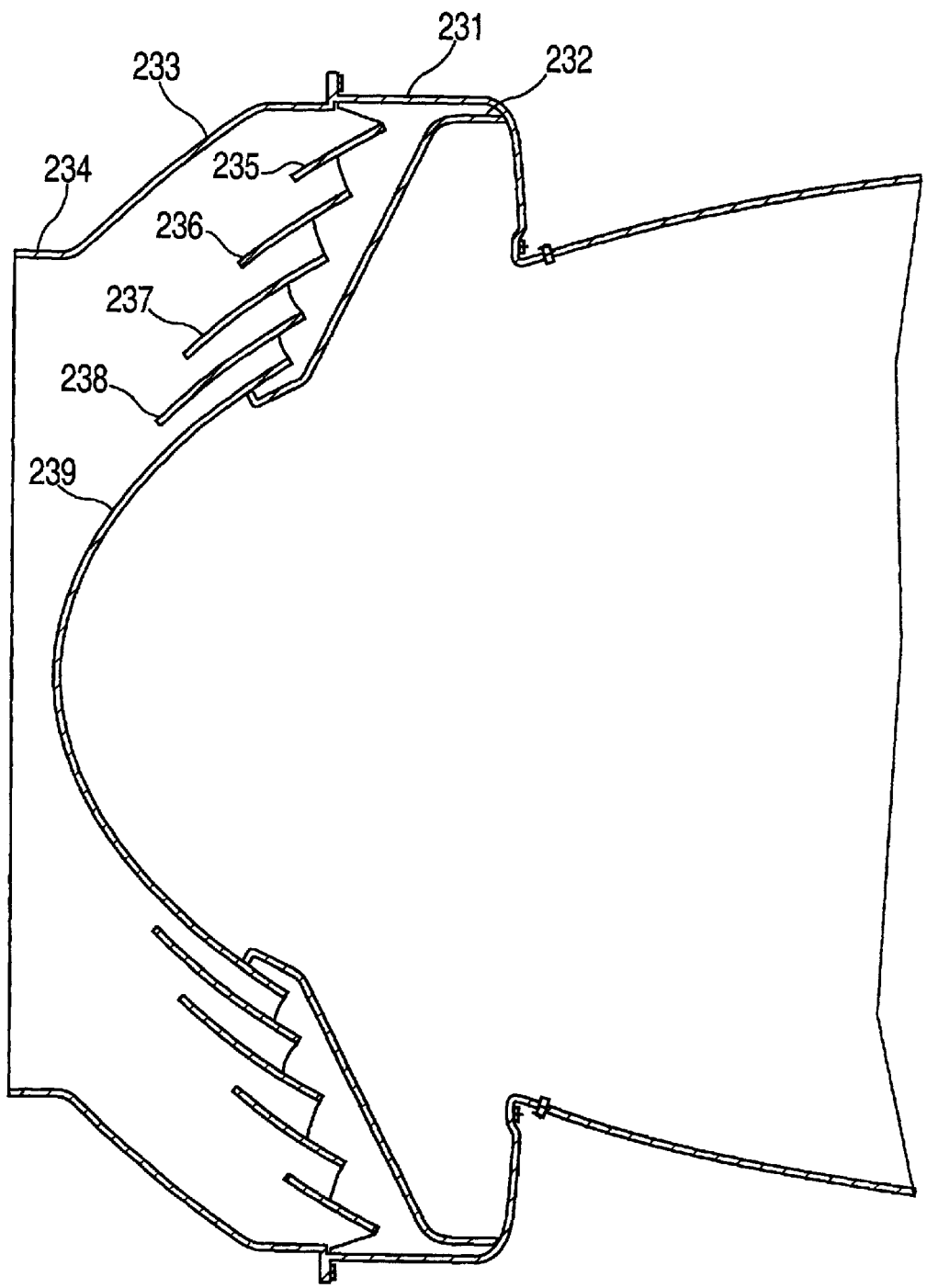
FIG. 5 is a partial enlarged view of one reflective grille of FIG. 3

In the embodiment of FIGS. 1 and 2, air passing through the duct system and into the chamber 10 must make a 180° turn around the end caps 23 and 24 to enter the chamber. This develops a back pressure which requires greater force to move air through the duct system. The present invention allows air to pass through the chamber 10 with the minimum diversion from a course along the chamber's major axis and less impediments to its free movement while, at the same time, not allowing UV energy to escape at the air inlet and outlet. In other words, the present system allows the passage of air almost unhindered in and out of the chamber 10, yet reflect substantially all the UV light back into the chamber 10 greatly reducing the energy requirements of the system. FIGS. 3, 4 and 5 disclose a chamber having a reflective grille structure of the present invention which accomplishes this end.

FIG. 3 is a cross-section of a germicidal air chamber with the new grille structure. Such grille configuration is equally useful in an air, water and combined air/water purification system where a central UV transparent conduit or pipe (not shown) may be positioned along the major axis of the chamber 10. End caps 23 and 24 are replaced with grilles 230 and 240 positioned in enlarged sections 231 and 241 of the chamber 10, all formed from UV reflective material.

The enlarged section 231 of the chamber 10 is formed from a cylindrical collar 232 and a truncated ellipsoidal section 233. The foci 250 of the truncated ellipsoidal section 233 is common with that of the chamber 10. The truncated ellipsoidal section 233 is joined with a second cylindrical collar 234 of reduced diameter which may mate with the duct 12 in which the unit is mounted or with an adapter (not shown) designed to mate it with the duct 12. Similarly, enlarged section 241 is formed from a cylindrical collar 242 and a truncated ellipsoidal section 243 having a cylindrical collar 244 for mating with the duct 12.

A grille is formed from a series of truncated sections of ellipsoids 235–239 and 245–249 having foci 250 and 251 common to the chamber 10 and with truncated ellipsoidal sections 233 and 243. As seen in FIG. 5, ellipsoidal grille elements 235–239 form a series of spatially separated steps having gaps in-between to allow the passage of air. The ellipsoidal grille elements 235–239 are held in place by fins 260–263. The center sections 239 and 249 forms a closed end of the chamber 10. The ellipsoidal grille elements 235–239 and 245–249, maintain reflective uniformity and common focal paths with the chamber 10, containing the light energy within the chamber 10. The spacing between the ellipsoidal grille elements 235–239 and 245–249, in combination with their surface length and positioning of the elements, is such that light energy coming directly from the ellipsoidal portion of chamber 10 hitting the surface of such grille 230 is reflected back into the chamber 10 as if there were only a single elliptical chamber.

The enlarged sections 231 and 241 are dimensioned so that the included angle of incident UV radiation is reflected back into the chamber 10 from any angle permitted by the chamber wall. The ellipsoidal grille elements 235–239 and 245–249 in combination with the inner surface of enlarged sections 231 and 241 act to reflect UV back into the chamber 10. Secondary reflections occurring between the ellipsoidal grille elements 235–239 and 245–249 tend to be reflected back into the chamber 10 by truncated ellipsoidal sections 233 and 243. Views into the chamber are equally blocked by the ellipsoidal grille elements 235–239 and 245–249.

The number of grille sections, their radial positioning and surface length are a function of the chamber 10 size and the desired air flow. The surface length of each ellipsoidal grille element 235–239 and 245–249 generally increases as their diameter and the radial spacing decreases.

FIG. 4 shows a view at plane A—A of FIG. 3. The ellipsoid grille elements 235–239 when viewed along the main axis of the ellipsoid chamber form a solid reflective wall and thus, act to reflect light back into the chamber nearly as efficiently as if there was a solid end cap while air is allowed to pass in the gap between the ellipsoid grille elements 235–239. In other words, the ellipsoid grille elements 235–239 and 245–249 form partially separated radial steps to provide air or fluid passage between them while containing UV radiation originating in the chamber 10. Ellipsoid grille elements 235–239 and 245–249 are held in place by struts 260, 261, 262 and 263.

The grille spacing is selected such that the cross-sectional area of the air passages between the ellipsoidal grille elements 235–239 and 245–249 is greater than that of the chamber 10 as truncated immediately before the enlarged sections 231 and 241, thereby compensating for the increased surface friction caused by the ellipsoidal grille elements 235–239 and 245–249, eliminating back pressure. In other words, the summation of the spacing between the ellipsoidal grille elements 235–239 and 245–249 is greater than the cross-section of the chamber as truncated immediately before the enlarged sections 231 and 241.

Figure 6:
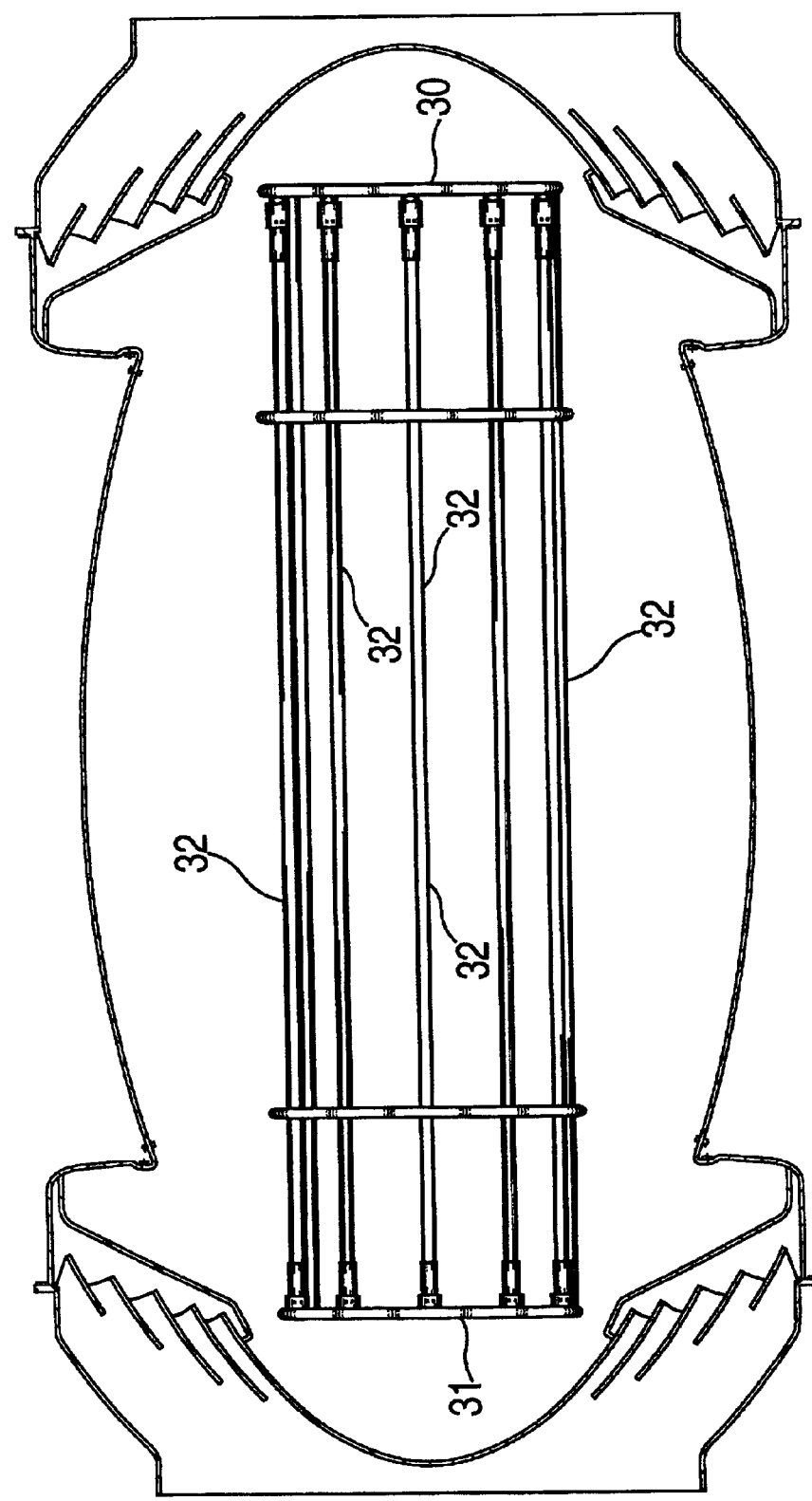
FIG. 6 is a cross-sectional view of the chamber of FIG. 3 having a multi-tube ultraviolet light source.

FIG. 6 discloses an array of linear UV tubes 32 between the ends 30 and 31. Due to the optic properties of the chamber 10, a UV light source positioned any place in the chamber 10 will result in a uniform distribution of energy throughout the chamber 10 and, thus, this lamp configuration, as any other lamp configuration, will result in a uniform distribution of light. However, the greater the distance traveled for any ray before its first reflection, incident with the wall, the more efficient the system since each reflection on the wall absorbs a certain amount of the UV energy. Thus, the most efficient system would have the light energy introduced at the geometric center of the ellipsoid chamber 10.

The lamps 32 of FIG. 6 would have a large portion of the emitted UV light reflected in a relatively short distance from the lamp with a resulting loss in efficiency. If lamp 32 were a standard 60" lamp with a surface area of 141 square inches, the equivalent ball shaped lamp would have a diameter of approx. 6.7 square inches and a cross sectional (fluid-flow-resistant profile) area of 35.25 square inches. Such a fluid resistance would not be acceptable in most applications for the present invention, not even taking into account that the present invention contemplates a number of lamps 32 in the chamber 10. A ball shape lamp is also impractical due to high temperatures generated in such a restricted configuration.

The solution is use of one or more long tube lamps coiled into a helix 50 located as close to the center of the chamber 10 as possible. A lamp of 60" length coiled into turn and a half of a helix will have a cross section of 14.28 square inches. A number of such helical lamps can be mounted end to end so as to spiral down the centerline of the chamber 10 and thereby minimize fluid resistance. Alternately a single extended lamp 50 may be used.

Figure 7:
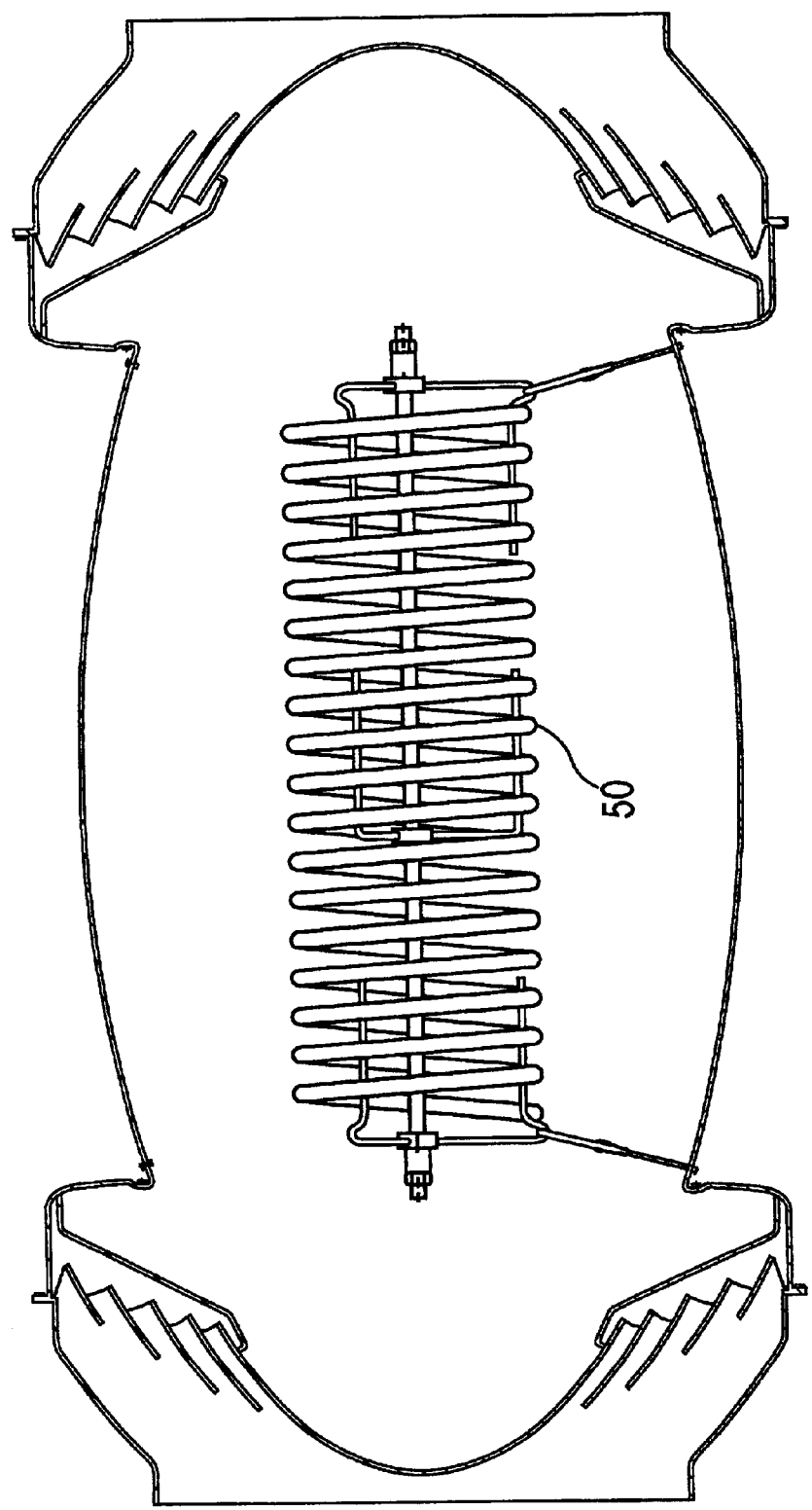
FIG. 7 is a cross-sectional view of the chamber of FIG. 3 having a content pitch helical ultraviolet light source.

FIG. 7 shows, a helical UV source 50 of equal pitch along its length positioned towards the center of the chamber along its central axis. Due to its helical shape, source 50 extends for a comparatively shorter length then the equivalent linear tubes shown in FIG. 6 and therefore would act to concentrate the UV source towards the center of the chamber. Thus, in turn lengthens the distance to the first reflection.

Figure 8:
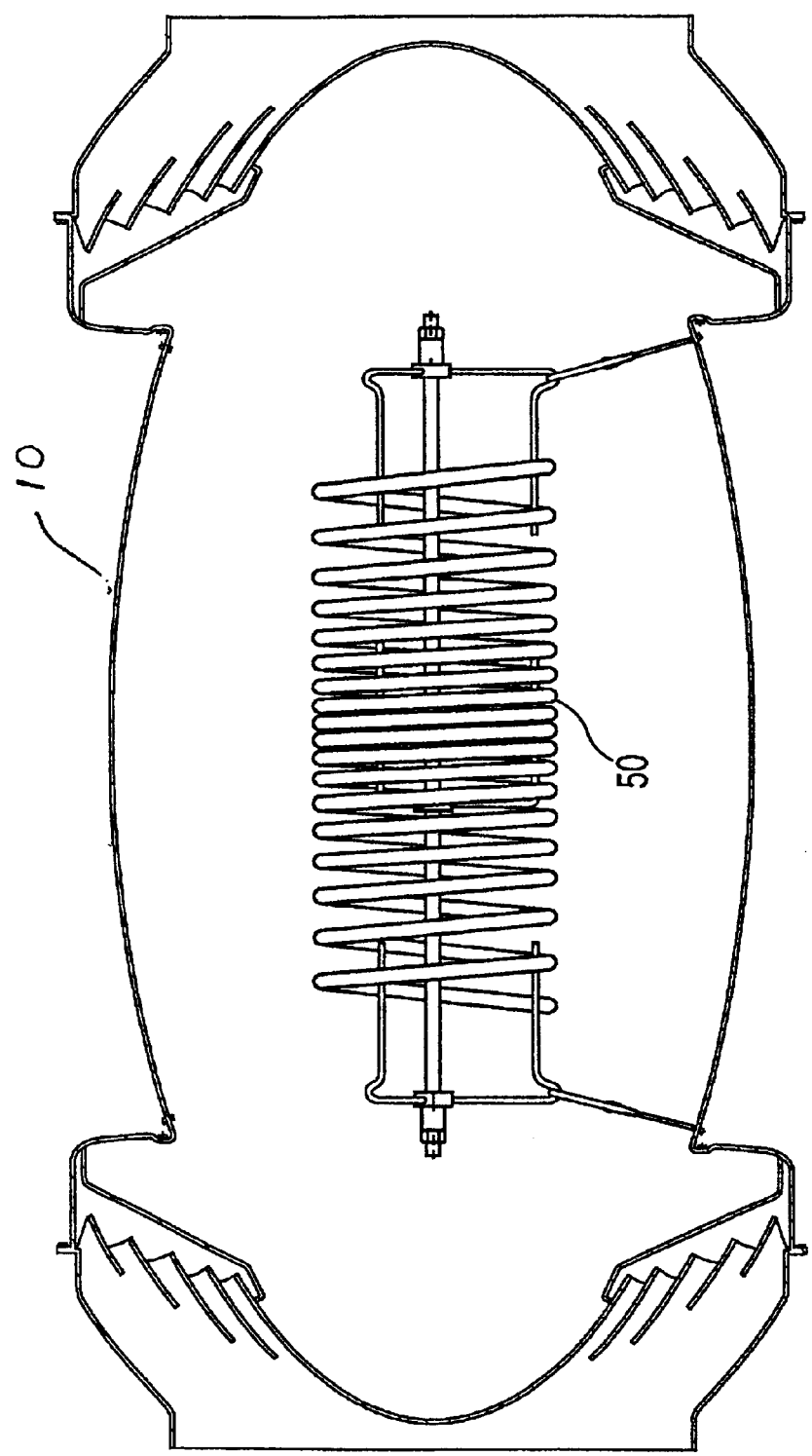
FIG. 8 is a cross section of the chamber of FIG. 3 having a variable pitch helical ultraviolet light source.

To further concentrate the light source in the chamber, a variable pitch helical light source 50 may be used, as shown in FIG. 8. In FIG. 8 the number of turns per inch at the center of the chamber is greater then those further from the center, further shortening the over all length of helical coil 50 and thus lengthening the path to first reflection. This helical formation is particularly useful in lighting a UV transparent fluid conduit positioned along the major axis of the chamber 10.

Figure 10:
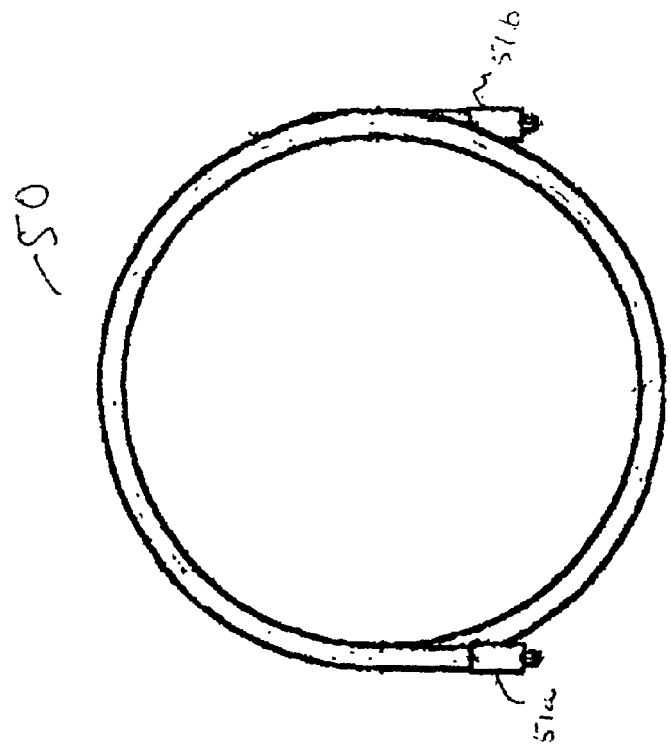
FIG. 10 is a side view of the lamp of FIG. 9
Figure 9:
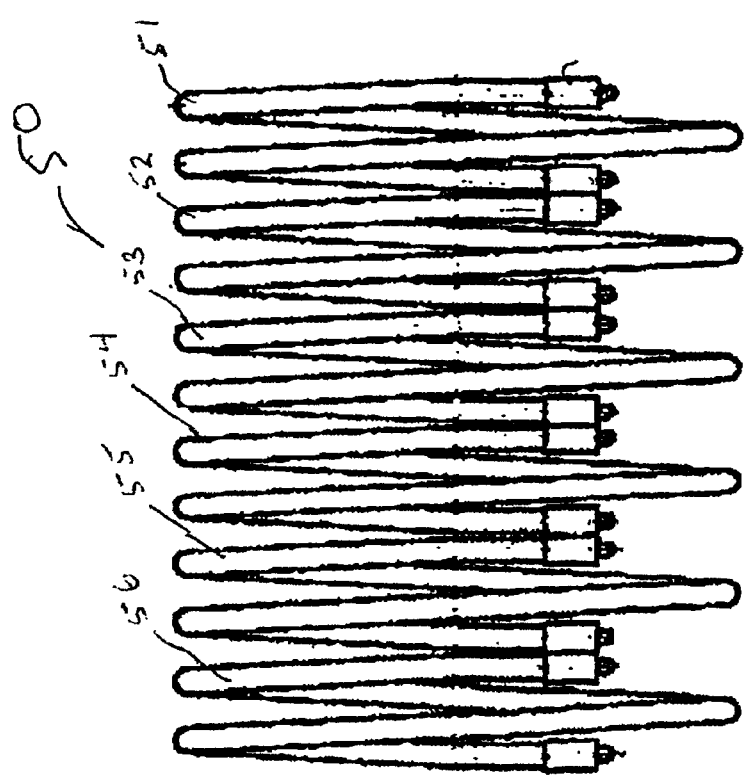
FIG. 9 is a front view of a helical light source formed from a number of one and a half turn UV lamps with their end caps aligned.
Figure 12:
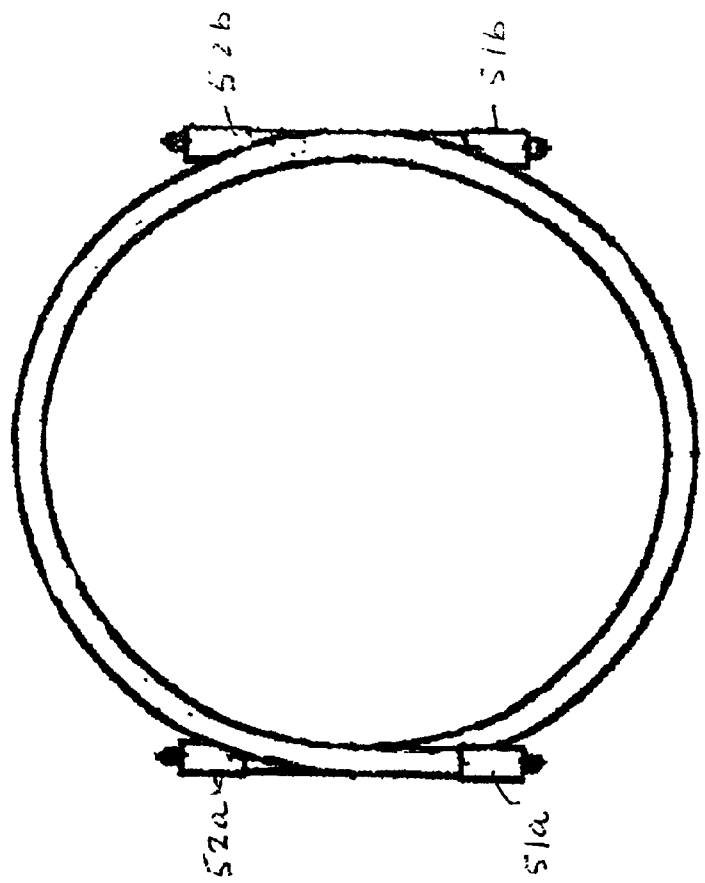
FIG. 12 is a side view of the helical lamp of FIG. 11
Figure 11:
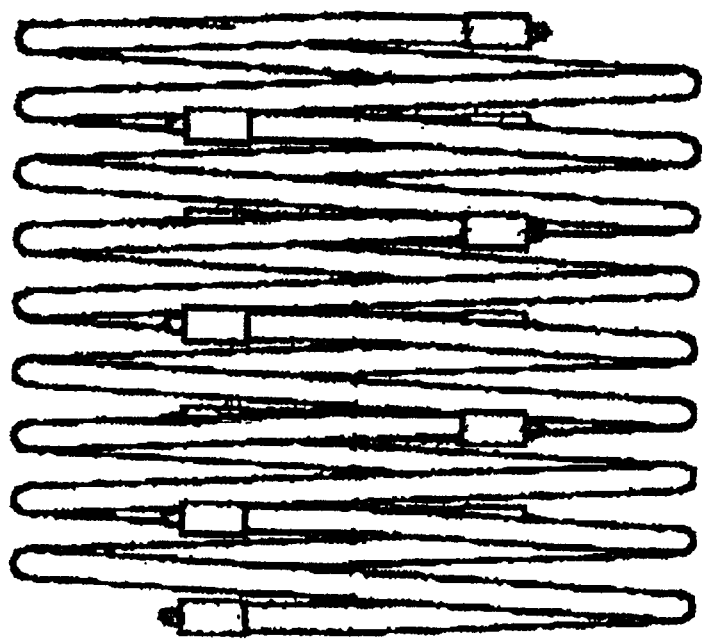
FIG. 11 is a front view of a helical lamp in accordance with the present invention in which the one and a half turn helical lamp are positioned with their end caps opposite from each other.
Figure 13:
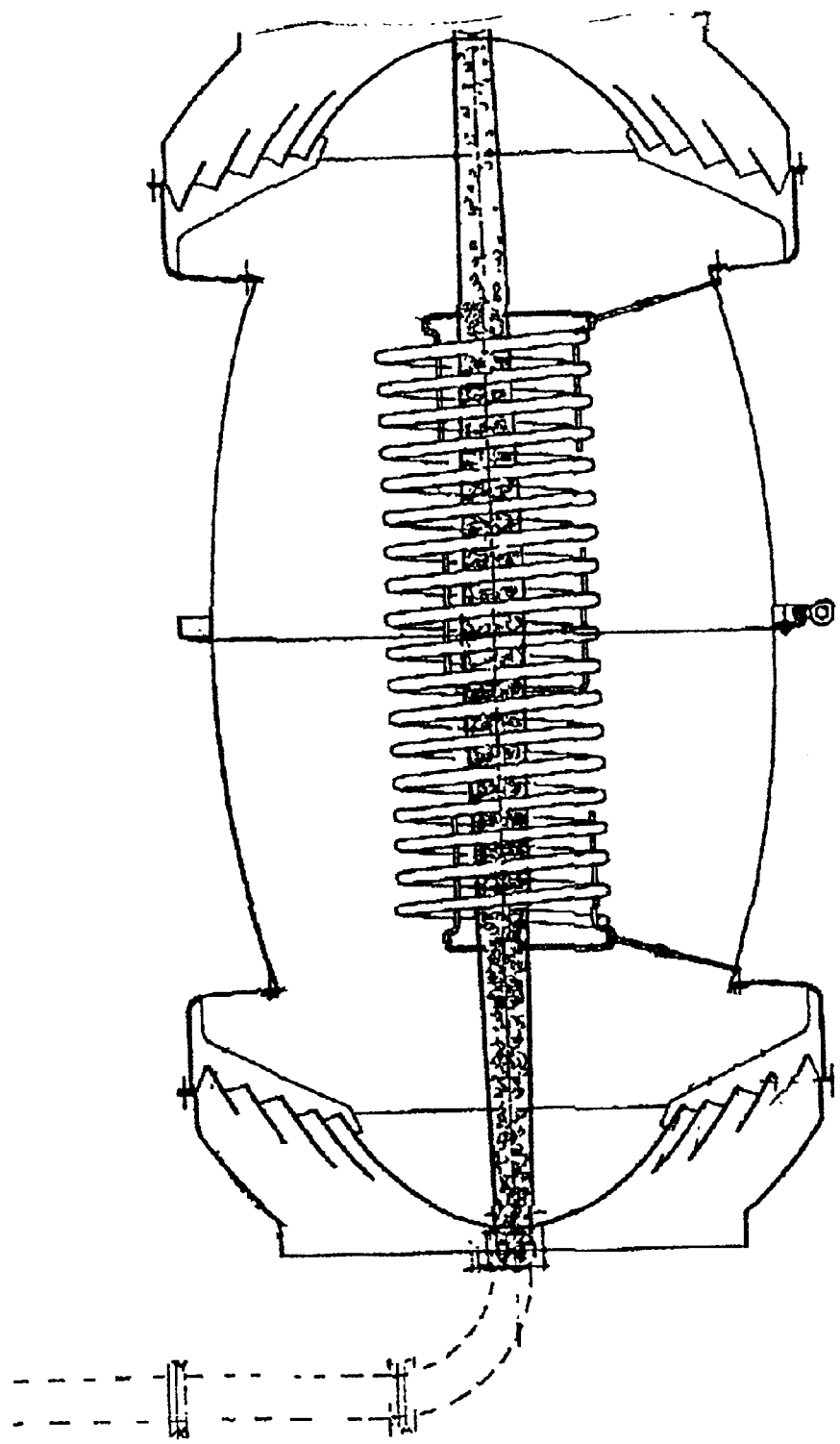
FIG. 13 is a cross view of chamber of FIG. 3 having a helical lamp with the fluid conduit passing through it.

While FIGS. 7 & 8 show the helical coil 50 as a single helical coil, several other configurations are possible to obtain the same result. The helical UV source 50 maybe composed of individual one and a half turns lamps 51 through 56 having connectors, 51a & b through 56a & b for electrical connection to an energy source. They can be connected in parallel by means of a connecting wire or track (not shown) running along each side of the helical lamp 50, shown in FIG. 9 and FIG. 10. Alternatively, as seen in FIGS. 11 & 12 the individual lamps 51 through 56 maybe positioned so that their connectors 51a &b–56(a&b) are positioned 180° from each other. This arrangement allows for greater compacting of the lamps. The two systems may be combined to produce a higher concentration of light source at the center by use of the configuration of FIG. 11 and a less intense source through use of configuration of FIG. 9 around the center of the chamber.

Figure 14:
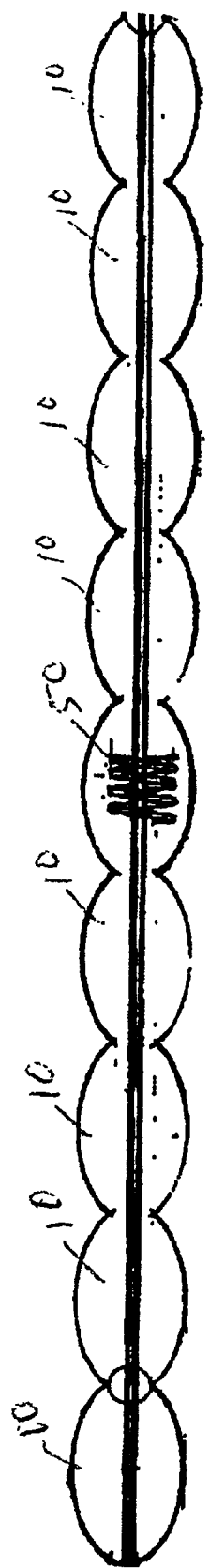
FIG. 14 is a view of interconnected chambers with a single helical lamp source in the center of the chamber.

FIG. 14 discloses the use of multiple chambers 10 interconnected to form a single unit with a single helical light source 50 in the center chamber, since a light source in one of a series of interconnected helical chambers will fill all of the chambers with uniform light. This configuration allows for dramatically long distances before the first reflection and thus the first energy lost, while providing uniform UV radiation throughout the chambers.

While the invention has been described as having a preferred design, it is understood that it is capable of further modification, uses and/or adaptations of the invention following in general principle of the invention and including such departures from the present disclosure as come within known or customary practice in the art to which the invention pertains, as may be applied to the central figures herein above set forth and fall within the scope of the invention of the limits of the appended claims.

I claim:

1. An apparatus for germicidally cleansing a gas comprising:

a chamber positioned in a duct system having an inlet opening to allow the gas to enter the chamber and a separate exit opening to allow air to exit the chamber;

a helical ultraviolet light source positioned in the chamber;

the internal walls of the chamber and grille being made from an ultraviolet reflective material and the walls of the chamber shaped to direct ultraviolet light into and upon the walls of the chamber uniformly throughout the chamber and such that the energy in the chamber accumulates over time to reach a uniform steady state energy level greater than that emitted by the UV source; and an adapter to mate the chamber with the duct system.

2. An apparatus according to claim 1, wherein a substantial portion of the chamber is in the shape of a truncated ellipsoid.

3. An apparatus according to claim 2, wherein the pitch of the helical ultraviolet light source is least at the center of the chamber and greatest at the points farthest from the center of the chamber.

4. An apparatus according to claim 3, wherein the ultraviolet light source is positioned along the major axis of the chamber.

5. An apparatus according to claim 4, wherein the ultraviolet light source is compose of a series of individual ultraviolet lamps which extend for one and a half turns each.

6. An apparatus according to claim 5, wherein the connectors of the lamps are aligned with each other.

7. An apparatus according to claim 4, wherein the connectors of the lamps are positioned 180 degrees from each other for each lamp.

8. An apparatus according to claim 4, wherein an ultraviolet transparent conduit is positioned along the major axis of the chamber inside the coils of the helical light source.

9. An apparatus according to claim 1, where in the helical ultraviolet light source is positioned in a UV transparent cylinder;

wherein the helical ultraviolet light source is not in direct contact with the gas or a fluid transported through the chamber.

* * * * *